US009849836B2

(12) United States Patent
Minikey, Jr. et al.

(10) Patent No.: US 9,849,836 B2
(45) Date of Patent: Dec. 26, 2017

(54) ROOF MOUNTED IMAGER MODULE

(71) Applicant: Gentex Corporation, Zeeland, MI (US)

(72) Inventors: Danny L. Minikey, Jr., Fenwick, MI (US); Richard T. Fish, Jr., Hudsonville, MI (US); Mark R. Roth, Grand Rapids, MI (US)

(73) Assignee: GENTEX CORPORATION, Zeeland, MI (US)

( * ) Notice: Subject to any disclaimer, the term of this patent is extended or adjusted under 35 U.S.C. 154(b) by 226 days.

(21) Appl. No.: 14/694,180

(22) Filed: Apr. 23, 2015

(65) Prior Publication Data
US 2015/0307026 A1    Oct. 29, 2015

Related U.S. Application Data

(60) Provisional application No. 61/983,713, filed on Apr. 24, 2014.

(51) Int. Cl.
*B60R 1/00* (2006.01)
*H01Q 1/12* (2006.01)
*H01Q 1/22* (2006.01)
*H01Q 1/32* (2006.01)
*B60R 11/04* (2006.01)
*H01Q 1/42* (2006.01)
(Continued)

(52) U.S. Cl.
CPC ............... *B60R 1/00* (2013.01); *B60R 11/04* (2013.01); *H01Q 1/1214* (2013.01); *H01Q 1/22* (2013.01); *H01Q 1/3275* (2013.01); *H01Q 1/42* (2013.01); *B60R 2011/004* (2013.01); *H04N 7/183* (2013.01)

(58) Field of Classification Search
CPC ..... B60R 1/00; B60R 11/04; B60R 2011/004; H04N 7/183
See application file for complete search history.

(56) References Cited

U.S. PATENT DOCUMENTS

| 4,063,258 A | 12/1977 | Allen |
| 4,621,785 A | 11/1986 | Embra |
| 5,619,036 A | 4/1997 | Salvio et al. |

(Continued)

FOREIGN PATENT DOCUMENTS

| EP | 1006486 A2 | 6/2000 |
| EP | 1227683 A1 | 7/2002 |

(Continued)

OTHER PUBLICATIONS

International Search Report and Written Opinion of the International Searching Authority, or the Declaration, dated Nov. 17, 2016, for International Application No. PCT/US2015/027282, filed on Apr. 23, 2015, 9 pages.

*Primary Examiner* — William C Vaughn, Jr.
*Assistant Examiner* — Lindsay Uhl
(74) *Attorney, Agent, or Firm* — Price Heneveld LLP; Bradley D. Johnson

(57) ABSTRACT

A roof mounted module for a vehicle includes an imager housing in secure engagement with a roof of the vehicle. The imager housing defines a lateral aperture and a vertical aperture. An imager is disposed in the imager housing and is in communication with the lateral aperture. An antenna housing is removably coupled to the imager housing and is in communication with the vehicle via a data connection that extends through the vertical aperture.

16 Claims, 9 Drawing Sheets

(51) Int. Cl.
　　　*H04N 7/18*　　　(2006.01)
　　　*B60R 11/00*　　　(2006.01)

(56) References Cited

U.S. PATENT DOCUMENTS

| | | |
|---|---|---|
| 5,760,828 A | 6/1998 | Cortes |
| 5,833,101 A | 11/1998 | Watkins |
| 6,333,759 B1 | 12/2001 | Mazzilli |
| 6,536,961 B1 | 3/2003 | Gillies |
| 6,580,373 B1 | 6/2003 | Ohashi |
| 7,111,996 B2 | 9/2006 | Seger et al. |
| 7,245,207 B1 * | 7/2007 | Dayan ............... B60R 11/0235 340/435 |
| 7,265,656 B2 | 9/2007 | McMahon et al. |
| 7,448,812 B2 | 11/2008 | Heibel |
| 7,499,100 B2 | 3/2009 | Miyazaki et al. |
| 7,609,961 B2 | 10/2009 | Park |
| 7,881,496 B2 | 2/2011 | Camilleri et al. |
| 7,883,064 B2 | 2/2011 | Luft et al. |
| 9,229,104 B2 * | 1/2016 | Klar ..................... G01S 13/931 |
| 2006/0238318 A1 | 10/2006 | Brouwer et al. |
| 2007/0236569 A1 | 10/2007 | Lin |
| 2009/0122141 A1 | 5/2009 | Nakamura et al. |
| 2010/0277379 A1 * | 11/2010 | Lindackers .......... H01Q 1/1207 343/713 |
| 2011/0317298 A1 | 12/2011 | van Stiphout |
| 2012/0327234 A1 * | 12/2012 | Fish, Jr. ................. B60R 11/04 348/148 |
| 2014/0111684 A1 * | 4/2014 | Corbin .................. H01Q 1/243 348/374 |

FOREIGN PATENT DOCUMENTS

| | | |
|---|---|---|
| KR | 100909368 B1 | 7/2009 |
| KR | 101134305 B1 | 4/2012 |
| KR | 101343814 B1 | 12/2013 |

* cited by examiner

ROOF MOUNTED IMAGER MODULE

CROSS-REFERENCE TO RELATED APPLICATION

This application claims priority to U.S. Provisional Application No. 61/983,713, filed on Apr. 24, 2014, entitled "ROOF MOUNTED IMAGER MODULE," the disclosure of which is hereby incorporated herein by reference in its entirety.

BACKGROUND OF THE DISCLOSURE

The present disclosure generally relates to an imager module, and more particularly relates to a roof mounted imager module for a vehicle.

SUMMARY OF THE PRESENT DISCLOSURE

One aspect of the present disclosure includes a roof mounted module for a vehicle including an imager housing in secure engagement with a roof of the vehicle. The imager housing defines a lateral aperture and a vertical aperture. An imager is disposed in the imager housing and is in communication with the lateral aperture. An antenna housing is removably coupled to the imager housing and is in communication with the vehicle via a data connection that extends through the vertical aperture.

Another aspect of the present disclosure includes a roof mounted antenna and imager module for a vehicle including an imager housing having a bottom side configured for secure engagement with a roof of the vehicle. An imager is disposed in the imager housing and is configured to capture image data through a window defined in the imager housing. An antenna housing is removably coupled to a top side of the imager housing.

Yet another aspect of the present disclosure includes a roof mounted module for a vehicle having an imager housing removably coupled with a roof of the vehicle. The imager housing includes a vertical aperture disposed through a rear wall thereof, and also includes a vertical aperture defined by a plurality of internal walls that extend from a bottom of the antenna housing to a lower wall of the imager housing, thereby separating an internal cavity of the imager housing from the vertical aperture. An imager is disposed in the imager housing and is in communication with the lateral aperture. An antenna housing is removably coupled to the imager housing and is in communication with the vehicle via a data connection that extends through the vertical aperture.

These and other aspects, objects, and features of the present disclosure will be understood and appreciated by those skilled in the art upon studying the following specification, claims, and appended drawings.

DETAILED DESCRIPTION OF EMBODIMENTS

Figure 1:
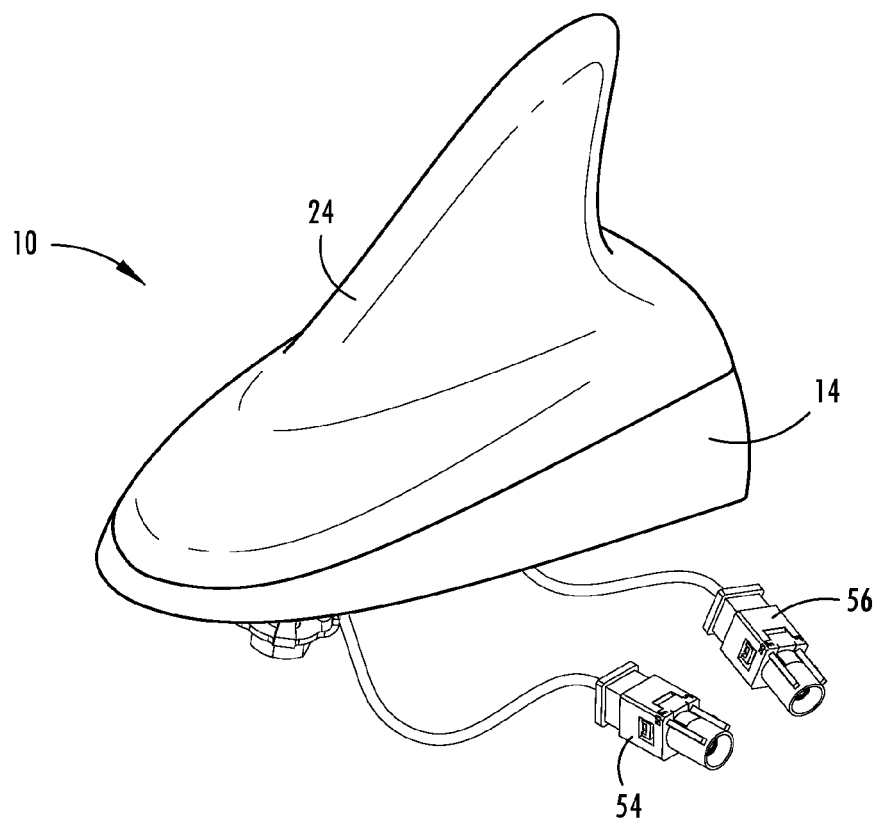
FIG. 1 is a top perspective view of one embodiment of a roof mounted antenna and imager module.

For purposes of description herein, the terms "upper," "lower," "right," "left," "rear," "front," "vertical," "horizontal," and derivatives thereof shall relate to the disclosure as oriented in FIG. 1. However, it is to be understood that the disclosure may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

Referring to FIGS. 1-12, reference numeral 10 generally designates a roof mounted module for a vehicle 12 including an imager housing 14 in secure engagement with a roof 16 of the vehicle 12. The imager housing 14 defines a viewing window 18 and a securing aperture 20. An imager 22 is disposed in the imager housing 14 and is in communication with the viewing window 18. An antenna housing 24 is removably coupled to the imager housing 14 and is in communication with the vehicle 12 via a data connection that extends through the securing aperture 20.

Figure 1A:
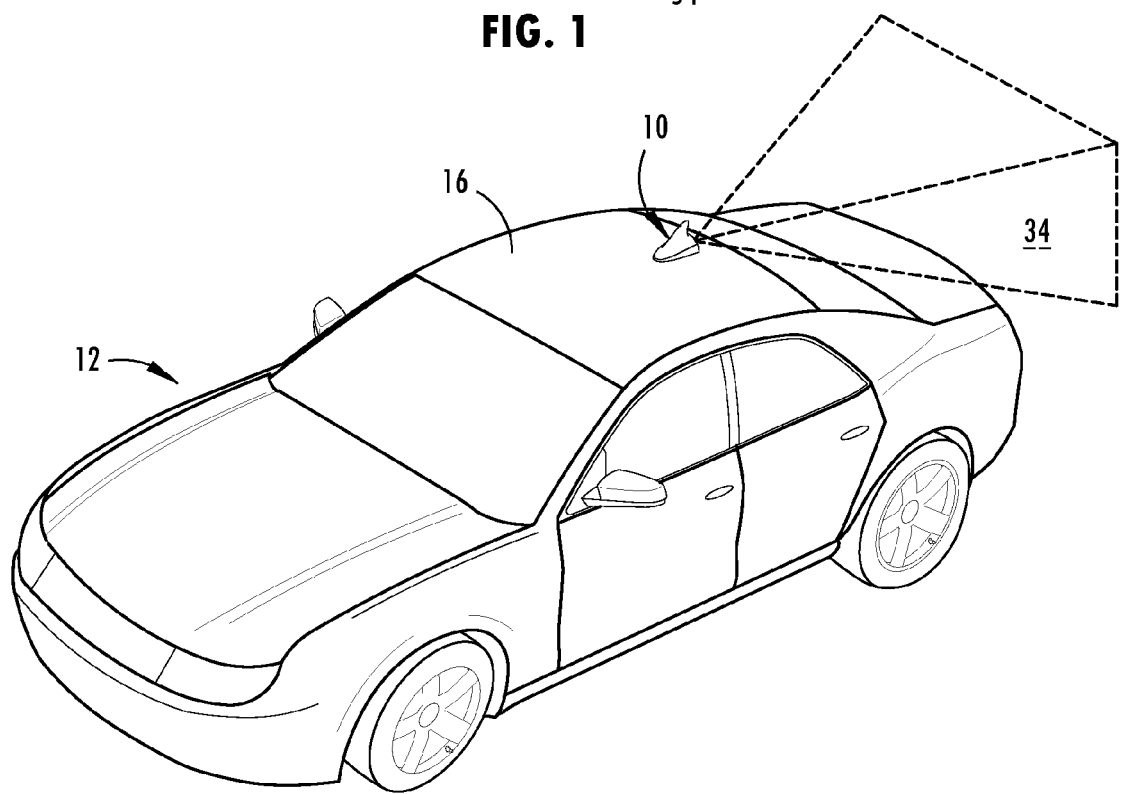
FIG. 1A is a top perspective view of the roof mounted antenna and imager module of FIG. 1 installed on a roof of a vehicle.
Figure 2:
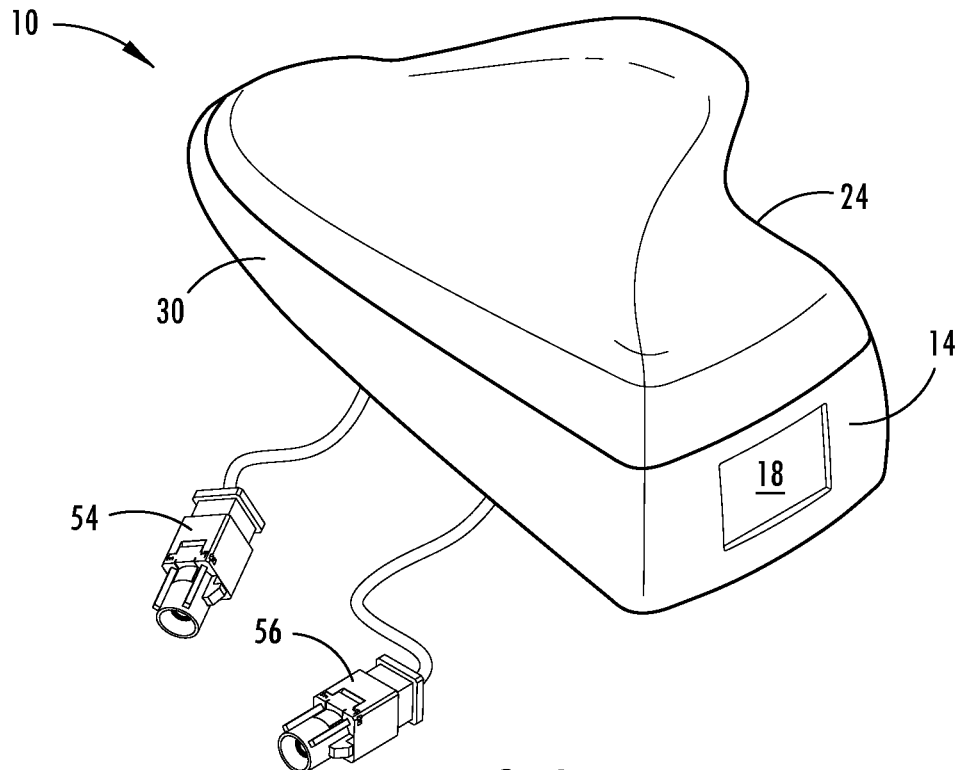
FIG. 2 is a rear top perspective view of the roof mounted antenna and imager module of FIG. 1.
Figure 3:
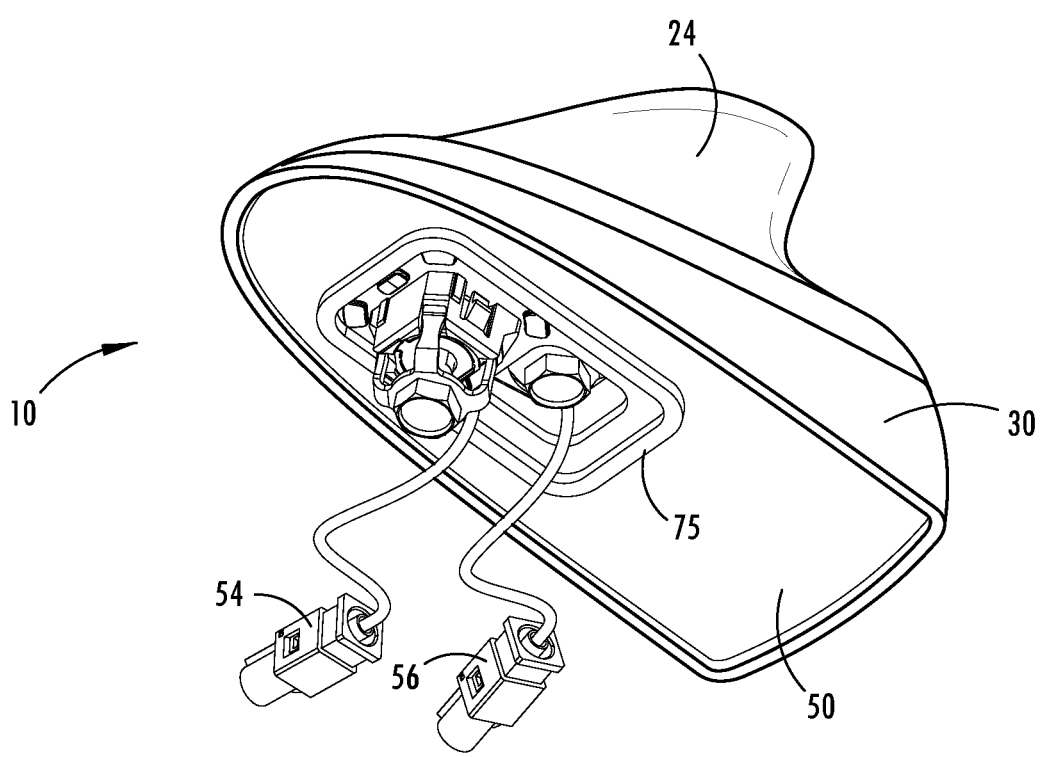
FIG. 3 is a bottom front perspective view of the roof mounted antenna and imager module of FIG. 1.
Figure 4:
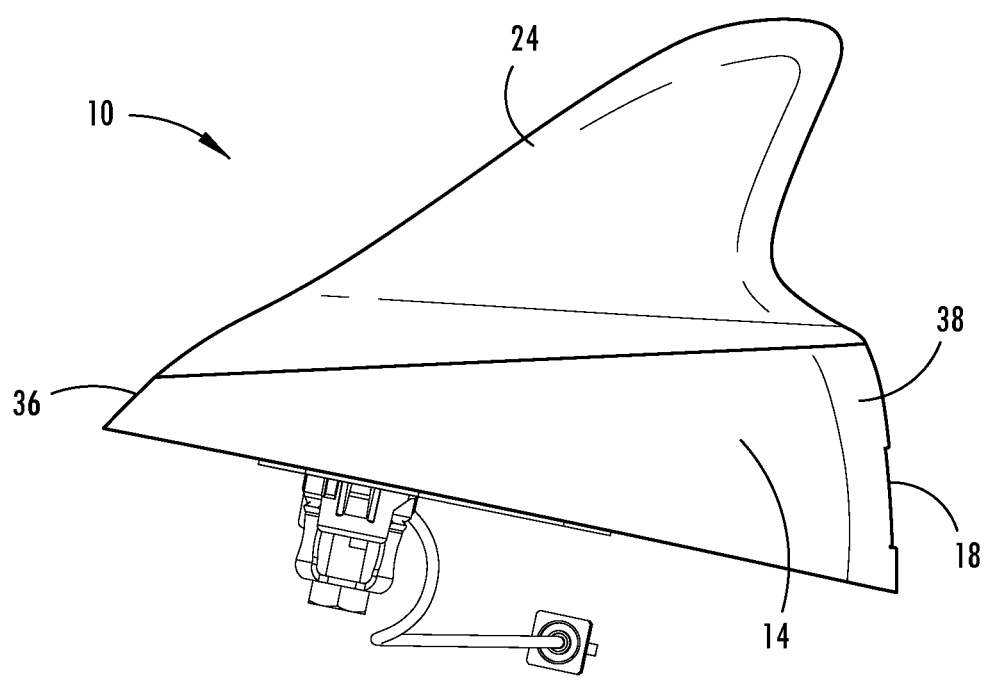
FIG. 4 is a side elevational view of the roof mounted antenna and imager module of FIG. 1.

With reference again to FIG. 1, the roof mounted module 10 is generally configured for installation on the roof 16 of the vehicle 12 as shown in FIG. 1A, but could be installed on any portion of the vehicle 12. The roof mounted module 10 generally has a smooth contoured exterior 30 that is aesthetically pleasing to consumers and also provides excellent aerodynamics, thereby minimizing any drag on the vehicle 12. In the illustrated embodiment shown in FIG. 1A, the viewing window 18 defined in the imager housing 14 is generally directed rearward such that the imager 22 disposed in the imager housing 14 can collect image data from a rear area 34 of the vehicle 12. However, it will be contemplated that the imager housing 14 or the viewing window 18 of the imager housing 14 can be directed in any direction on the vehicle 12 such that image data can be taken anywhere around the vehicle 12. Notably, as illustrated in FIGS. 1, 2, and 4, the transition from the imager housing 14 to the antenna housing 24 is generally continuous or flush such that the seam defined between the imager housing 14 and the antenna housing 24 is largely unnoticeable. Further, as is generally illustrated in FIG. 4, the imager housing 14 includes a tapered construction. More specifically, the imager housing 14 includes a front side 36 with a height that is less than a height of a rear side 38 of the imager housing 14. As illustrated, the peripheral dimensions of a top side of the imager housing 14 are substantially equal to the peripheral dimensions of a bottom side of the antenna housing 24.

Figure 5:
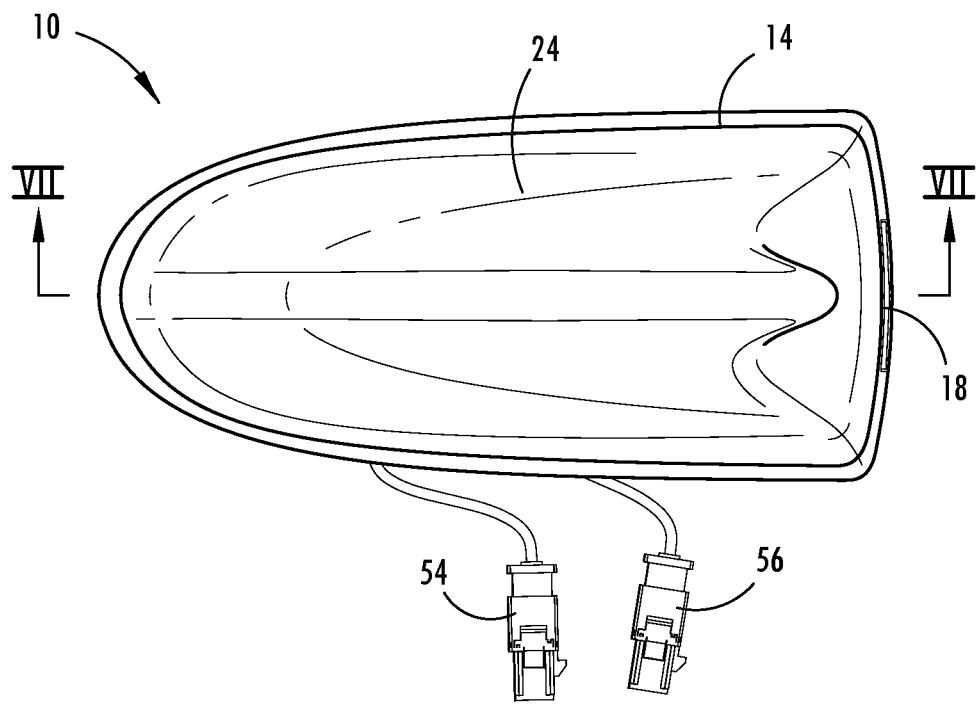
FIG. 5 is a top plan view of the roof mounted antenna and imager module of FIG. 1.
Figure 6:
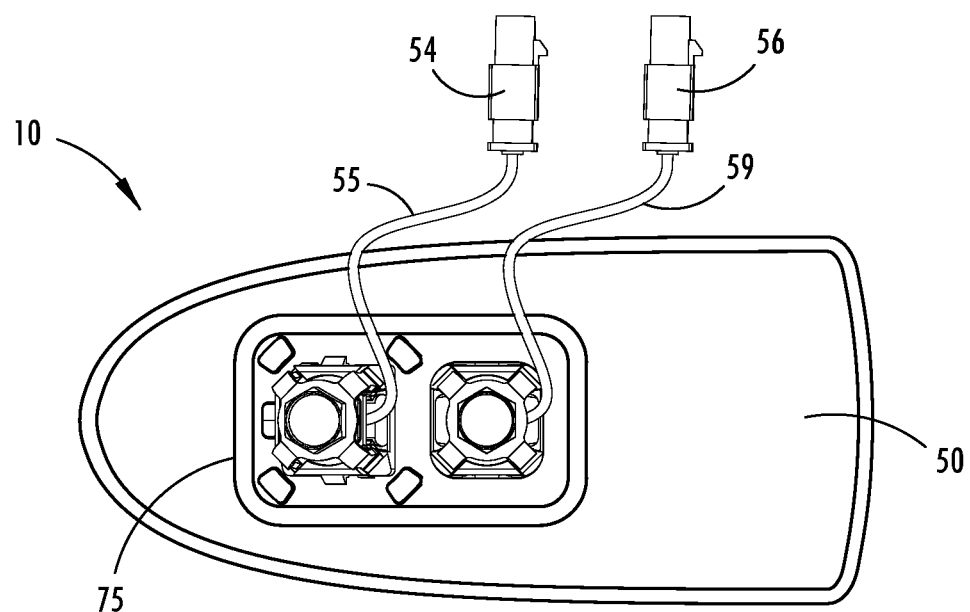
FIG. 6 is a bottom plan view of the roof mounted antenna and imager module of FIG. 1.

With reference to FIGS. 5 and 6, the external surfaces of the antenna housing 24 and the imager housing 14 are largely symmetrical along line VII-VII. Additionally, the external surfaces are gradually curved, which as noted above, provides aerodynamic qualities that minimize or eliminate any drag associated with the roof mounted module 10. As will be further explained herein, the same interface that can be used to connect the antenna housing 24 directly to the vehicle 12 can also be used to connect the antenna housing 24 to the imager housing 14. Accordingly, additional parts or interface connections are unnecessary. Stated differently, the imager housing 14 is configured to be installed between the antenna housing 24 and the roof 16 of the vehicle 12.

As generally illustrated in FIGS. 6-9, the imager housing 14 includes a lower wall 50 and an upper wall 52 and conceals the imager 22. An imager connector 54 is operably coupled with the imager, and in one embodiment, has a power and data cable 55 that extends through the securing aperture 20 of the imager housing 14, such that the imager connector 54 is in communication with the vehicle 12. Notably, the imager connector 54 does not necessarily have to pass through the securing aperture 20. However, regardless of how the imager connector 54 is routed, the imager connector 54 will be in communication with the vehicle 12. The imager connector 54 allows for a power and data connection to be made between the imager housing 14 and the vehicle 12. In addition, the securing aperture 20 that passes through the imager housing 14 is configured to receive an antenna connector 56 operably coupled with an antenna 57 disposed in the antenna housing 24. The antenna connector 56 provides a power and data connection from the vehicle 12 to the antenna 57 through a power and data cable 59.

With reference again to FIGS. 7-9, the antenna housing 24 includes a bottom wall 60 defining a support plate that is configured to support the antenna 57 disposed inside the antenna housing 24. The antenna connector 56 extends through the bottom wall 60 and through the securing aperture 20 in the imager housing 14. A gasket 58 extends around the antenna connector 56 below the bottom wall 60. One or more mechanical fasteners can be used to secure the antenna housing 24 to the upper wall 52 of the imager housing 14. The lower wall 50 of the imager housing 14 acts as a support plate that is configured to support a lateral circuit board 62 operably coupled with a ribbon connector 64 to a vertical circuit board 66. The vertical circuit board 66 is coupled with the imager 22 disposed between the vertical circuit board 66 and a cover lens 70. The lower wall 50 of the imager housing 14 also includes a base aperture 72 configured to relay the data and power cable from the antenna through the securing aperture 20, and also to relay a data and power cable from the imager 22 disposed in the imager housing 14. Gasket members 75 help seal the roof mounted module 10 against the roof 16 of the vehicle 12. It is also contemplated that an electromagnetic shield could be positioned inside the imager housing 14 to minimize or eliminate interference that could develop from the antenna and affect the imager 22.

Figure 7:
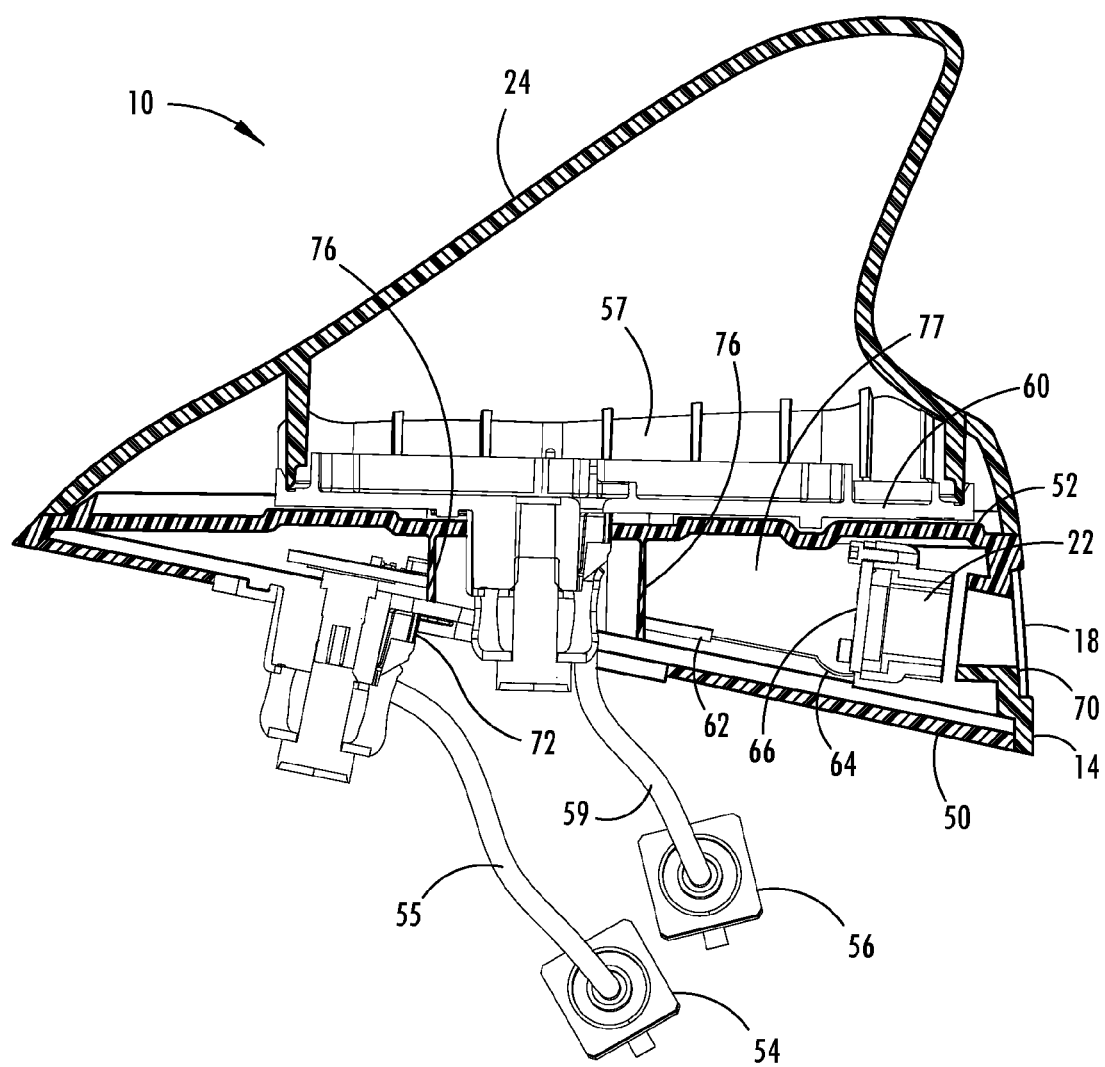
FIG. 7 is a side elevational cross-sectional view of the roof mounted antenna and imager module of FIG. 1 taken at line VII-VII.
Figure 8:
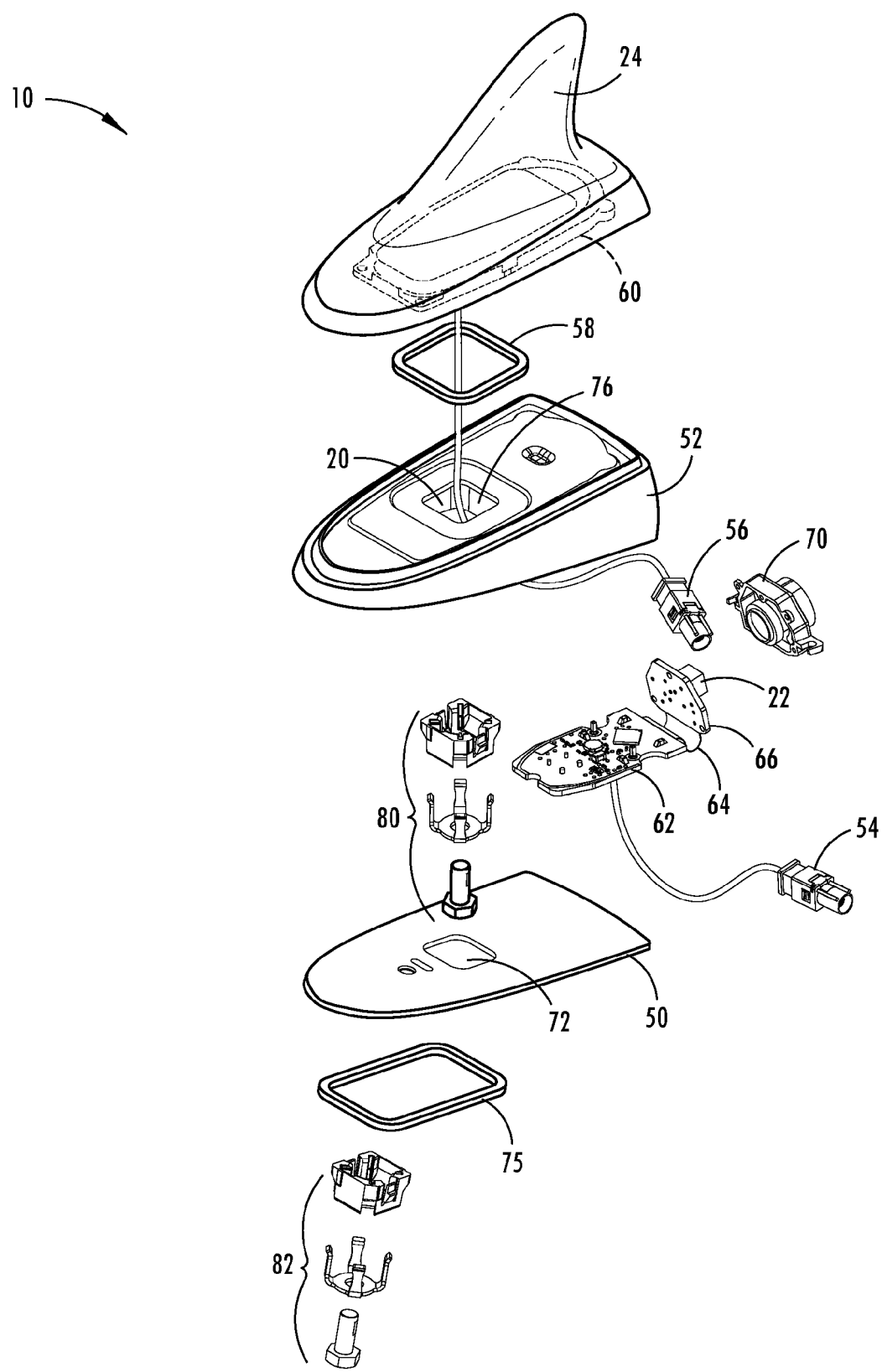
FIG. 8 is a top perspective exploded view of the roof mounted antenna and imager module of FIG. 1.
Figure 9:
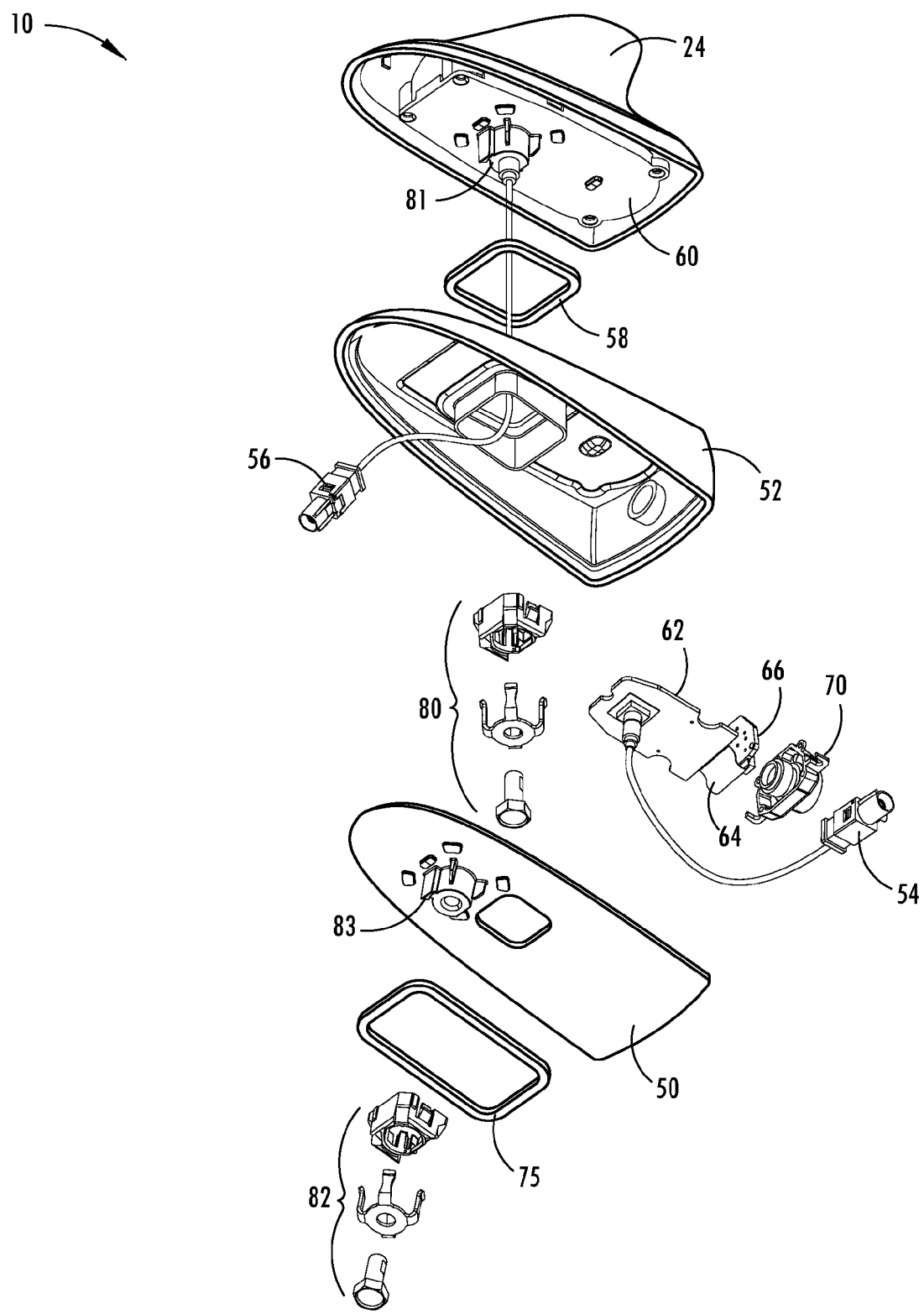
FIG. 9 is a bottom perspective exploded view of the roof mounted antenna and imager module of FIG. 1.

The securing aperture 20, as shown in FIGS. 7 and 8, is generally defined, at least partially, by a plurality of internal walls 76 that extend between the upper wall 52 and the lower wall 50. In one embodiment, it is contemplated that the internal walls 76 separate an internal cavity 77 of the imager housing 14 from the securing aperture 20. As a result, the components of the antenna housing 24 and the imager housing 14 can operate completely separately with little or no data or power interface. It is contemplated that the antenna connector 56 can pass through the vertical aperture 78 and the internal components of the imager housing 14 will be protected therefrom. In the illustrations provided in FIGS. 7 and 8, the securing aperture 20 is a generally vertical aperture.

With reference again to FIGS. 8 and 9, a mechanical fastening arrangement 80 and downwardly extending tower 81 generally secure the antenna housing 24 to the imager housing 14. The construction of the mechanical fastening arrangement 80 and downwardly extending tower 81 is the same or similar to a mechanical fastening arrangement 82 and a downwardly extending tower 83 that secures the imager housing 14 to the roof 16 of the vehicle 12. Accordingly, additional parts or interface components are not necessary to secure the imager housing 14 between the antenna housing 24 and the roof 16 of the vehicle 12.

Figure 10:
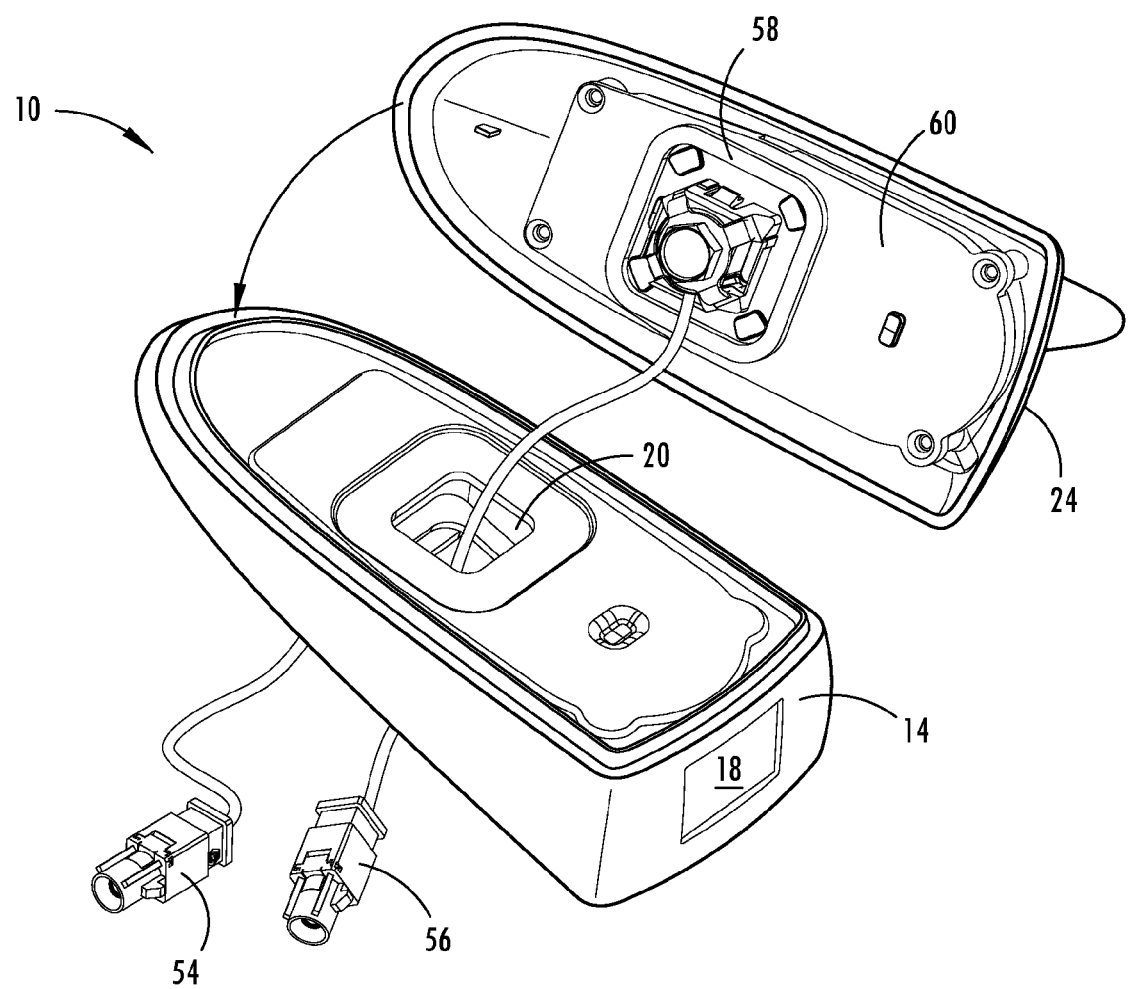
FIG. 10 is a top perspective view of an antenna housing and an imager housing prior to assembly.

As illustrated in FIG. 10, the antenna housing 24 is configured for direct engagement with the imager housing 14. As illustrated, a bottom side of the imager housing 14 is larger than a top side of the imager housing 14, and is also larger than a bottom side 84 of the antenna housing 24. The antenna housing 24 can be easily secured with the imager housing 14 and a watertight seal can be maintained therewith to prevent any damage to the imager 22 and the antenna located inside the imager housing 14 and the antenna housing 24, respectively. Alternatively, if the antenna is not desired on the vehicle 12, a cover plate may be secured on the upper wall 52 of the imager housing 14, such that only the imager housing 14 is directly connected to the vehicle 12, and consequently, the antenna is not in use. Alternatively, the imager housing 14 can be removed and the antenna housing 24 can be directly secured to the roof 16 of the vehicle 12.

Figure 11:
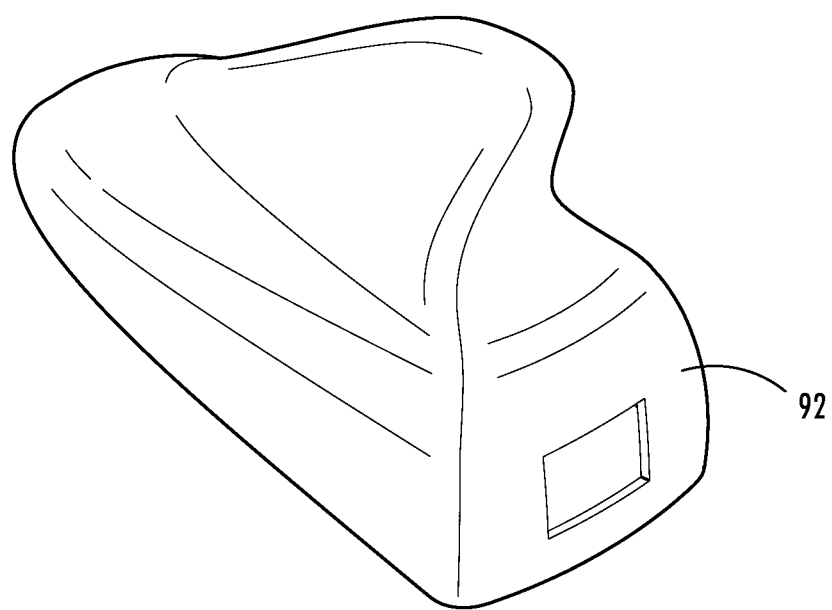
FIG. 11 is a top perspective view of an antenna housing cover shield.
Figure 12:
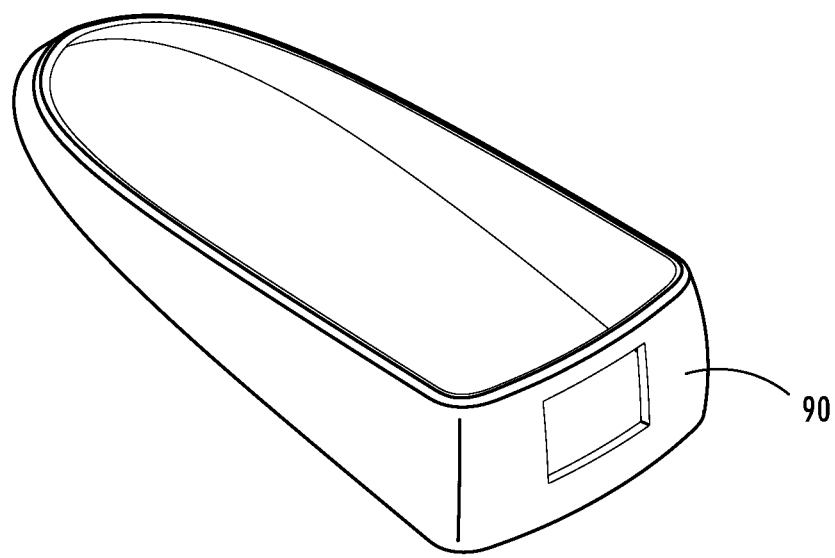
FIG. 12 is a top perspective view of an imager housing cover shield.

With reference to FIGS. 11 and 12, it is also contemplated that the roof mounted module 10 could include a cover shield 90 that covers only the imager housing 14 (FIG. 12), or a cover shield 92 that covers the antenna housing 24 (FIG.

11), or a cover shield that covers both. The cover shields are designed to provide an aesthetic treatment that may be color matched to the roof 16 of the vehicle 12.

The roof mounted antenna and imager module concepts, as set forth herein, are generally configured to provide a versatile system that allows for different antenna components and housings to be paired with different imager components and housings. This configuration enables an automotive manufacturer the ability to offer different imager and/or antenna options or packages utilizing the same basic housings. Accordingly, uniformity across various product offerings can be maintained. For example, the automotive manufacturer can pair "premium," "standard," and "base" model vehicles with corresponding "premium," "standard," and "base" roof mounted modules, such as those described above. Further, in an automotive manufacturing facility that produces multiple vehicles, the facility can receive a single imager housing that includes hardware and software to support any of a variety of imager/antenna combinations such that any number of interchangeable roof mounted modules can be provided to the consumer. The modules shown and described herein offer advantages to receiving and inventory departments of Original Equipment Manufacturers (OEM) with substantial versatility and flexibility.

The present disclosure may be used with a rearview assembly such as that described in U.S. Pat. Nos. 8,925,891; 8,814,373; 8,201,800; and 8,210,695; U.S. Patent Application Publication Nos. 2014/0063630, now U.S. Pat. No. 9,174,577, and 2012/0327234; and U.S. Provisional Patent Application Nos. 61/709,716; 61/707,676; and 61/704,869, which are hereby incorporated herein by reference in their entirety. Further, the present disclosure may be used with a rearview packaging assembly such as that described in U.S. Pat. Nos. 8,885,240; 8,814,373; 8,646,924; 8,643,931; and 8,264,761; and U.S. Provisional Patent Application Nos. 61/707,625 and 61/590,259, which are hereby incorporated herein by reference in their entirety. Additionally, it is contemplated that the present disclosure can include a bezel such as that described in U.S. Pat. Nos. 8,827,517; 8,210,695; and 8,201,800, which are hereby incorporated herein by reference in their entirety.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

What is claimed is:

1. A roof mounted module for a vehicle comprising:
   an imager housing in secure engagement with a roof of the vehicle, the imager housing defining a lateral aperture and a vertical aperture;
   an imager disposed in the imager housing and in communication with the lateral aperture; and
   an antenna housing removably coupled to the imager housing an in communication with the vehicle via a data connection that extends through the vertical aperture, wherein the vertical aperture is at least partially defined by a plurality of internal walls that extend from a bottom of the antenna housing to a lower wall of the imager housing, such that the data connection extends through the vertical aperture without extending into the imager housing.

2. The roof mounted module of claim 1, wherein the lateral aperture defines a viewing window that extends through a rear wall of the imager housing.

3. The roof mounted module of claim 2, further comprising:
   a clear polymeric cover lens extending over the viewing window and generally flush with the rear wall of the imager housing.

4. The roof mounted module of claim 1, wherein the imager housing includes a bottom side that engages the roof of the vehicle and a top side that engages a bottom side of the antenna housing.

5. The roof mounted module of claim 4, wherein the bottom side of the imager housing is larger than the bottom side of the antenna housing.

6. The roof mounted module of claim 1, wherein the imager is operably coupled to a vertical circuit board disposed behind the imager, and further wherein the vertical circuit board is operably coupled to a lateral circuit board adjacent the lower wall by a ribbon connector.

7. A roof mounted antenna and imager module for a vehicle, comprising:
- an imager housing including a bottom side configured for secure engagement with a roof of a vehicle;
- an imager disposed in the imager housing and configured to capture image data through a window defined in the imager housing; and
- an antenna housing removably coupled to a top side of the imager housing, wherein the antenna housing includes an antenna having a data cable that extends through a vertical aperture in the imager housing, the vertical aperture being at least partially defined by a plurality of internal walk that extend from a bottom of the antenna housing to a lower wall of the imager housing, thereby separating an internal cavity of the imager housing from the vertical aperture.

8. The roof mounted antenna and imager module of claim 7, wherein the window is disposed on a rear wall of the imager housing.

9. The roof mounted antenna and imager module of claim 7, further comprising:
- a vertical aperture defined in the imager housing, wherein a data connection between the vehicle and the antenna extends through the vertical aperture.

10. The roof mounted antenna and imager module of claim 7, wherein peripheral dimensions of a top side of the imager housing are equal to peripheral dimensions of a bottom side of the antenna housing.

11. A roof mounted module for a vehicle comprising:
- an imager housing removably coupled with a roof of the vehicle, the imager housing including a lateral aperture disposed through a rear wall thereof, and further including a vertical aperture defined by a plurality of internal walls that extend from a bottom of the antenna housing to a lower wall of the imager housing, thereby separating an internal cavity of the imager housing from the vertical aperture, such that the data connection extends through the vertical aperture and is electrically isolated from electrical connection with the imager housing;
- an imager disposed in the imager housing and in communication with a lateral aperture; and
- an antenna housing removably coupled to the imager housing and in communication with the vehicle via a data connection that extends through the vertical aperture.

12. The roof mounted module of claim 11, wherein the lateral aperture defines a viewing window that extends through the rear wall of the imager housing.

13. The roof mounted module of claim 12, further comprising:
- a clear polymeric cover lens extending over the viewing window and generally flush with the rear wall of the imager housing.

14. The roof mounted module of claim 11, wherein the imager housing includes a bottom side that engages the roof of the vehicle and a top side that engages a bottom side of the antenna housing.

15. The roof mounted module of claim 14, wherein the bottom side of the imager housing is larger than the bottom side of the antenna housing.

16. The roof mounted module of claim 11, wherein the imager is operably coupled to a vertical circuit board disposed behind the imager, and further wherein the vertical circuit board is operably coupled to a lateral circuit board adjacent the lower wall by a ribbon connector.

\* \* \* \* \*

UNITED STATES PATENT AND TRADEMARK OFFICE
CERTIFICATE OF CORRECTION

| | |
|---|---|
| PATENT NO. | : 9,849,836 B2 |
| APPLICATION NO. | : 14/694180 |
| DATED | : December 26, 2017 |
| INVENTOR(S) | : Minikey, Jr. et al. |

It is certified that error appears in the above-identified patent and that said Letters Patent is hereby corrected as shown below:

Column 6, Claim 1, Line 42:
"an" should be --and--;

Column 7, Claim 7, Line 14:
"walk" should be --walls--.

Signed and Sealed this
Thirteenth Day of March, 2018

Andrei Iancu
*Director of the United States Patent and Trademark Office*